United States Patent [19]

Hobson

[11] Patent Number: 4,667,504

[45] Date of Patent: May 26, 1987

[54] FLOW THROUGH DEVICE FOR DETERMINATION OF THE PENETRATION RATE OF CHEMICALS ACROSS BIOLOGICAL MEMBRANES IN VITRO

[75] Inventor: David W. Hobson, Columbus, Ohio

[73] Assignee: The United States of America as represented by the Secretary of the Air Force, Washington, D.C.

[21] Appl. No.: 914,410

[22] Filed: Oct. 2, 1986

[51] Int. Cl.$^4$ ............................................. G01N 13/00
[52] U.S. Cl. ........................................ 73/38; 73/64.3; 210/321.2
[58] Field of Search ................ 73/38, 64.3; 210/321.2, 210/644, 645

[56] References Cited

U.S. PATENT DOCUMENTS 4,594,884 6/1986 Bondi et al. ......................... 73/64.3

*Primary Examiner*—Stewart J. Levy
*Assistant Examiner*—Hezron E. Williams
*Attorney, Agent, or Firm*—Fredric L. Sinder; Donald J. Singer

[57] ABSTRACT

An apparatus for determining in vitro the penetration rate of chemicals across a biological membrane. The apparatus comprises two housings, one holding a reservoir of test chemical, and the other providing a chamber for flowing receptor solution across a membrane held in a membrane holding compartment. The membrane holding compartment comprises a cylindrical depression surrounding an open end of the receptor solution chamber. The receptor solution chamber is tilted slightly with its higher end open to the membrane holding compartment. The tilt prevents bubbles in the receptor solution from becoming stalled or trapped inside the chamber and interfering with the reliability and reproducibility of tests. An inlet bore from the upper surface of the receptor housing leads to a closed end of the chamber inside the receptor housing. An outlet bore leads from the top of the open end of the chamber near the membrane holding compartment to the upper surface of the receptor housing. The inlet bore is sized smaller than the outlet bore. The depth of the depression forming the membrane holding compartment varies, tapering from a lesser depth at its intersection with the chamber to a greater depth at the outer circumference of the depression. The thus-formed truncated cone ensures that a sample biological membrane is stretched taut over the chamber opening by the force fastening the reservoir housing to the receptor solution housing. The invention includes the method taught by the disclosed apparatus.

10 Claims, 3 Drawing Figures

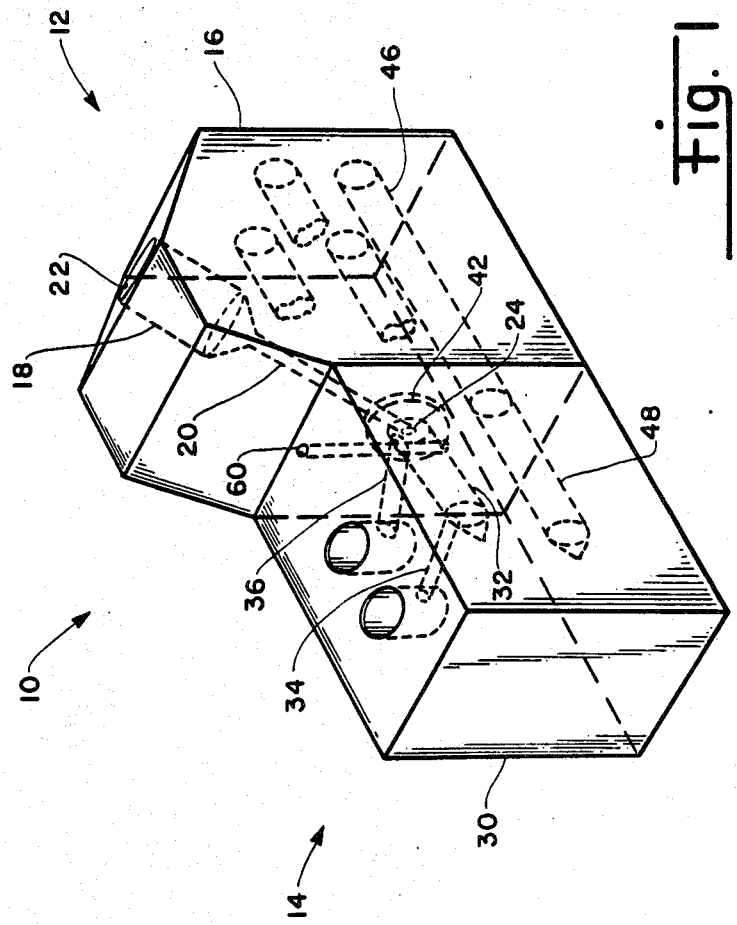

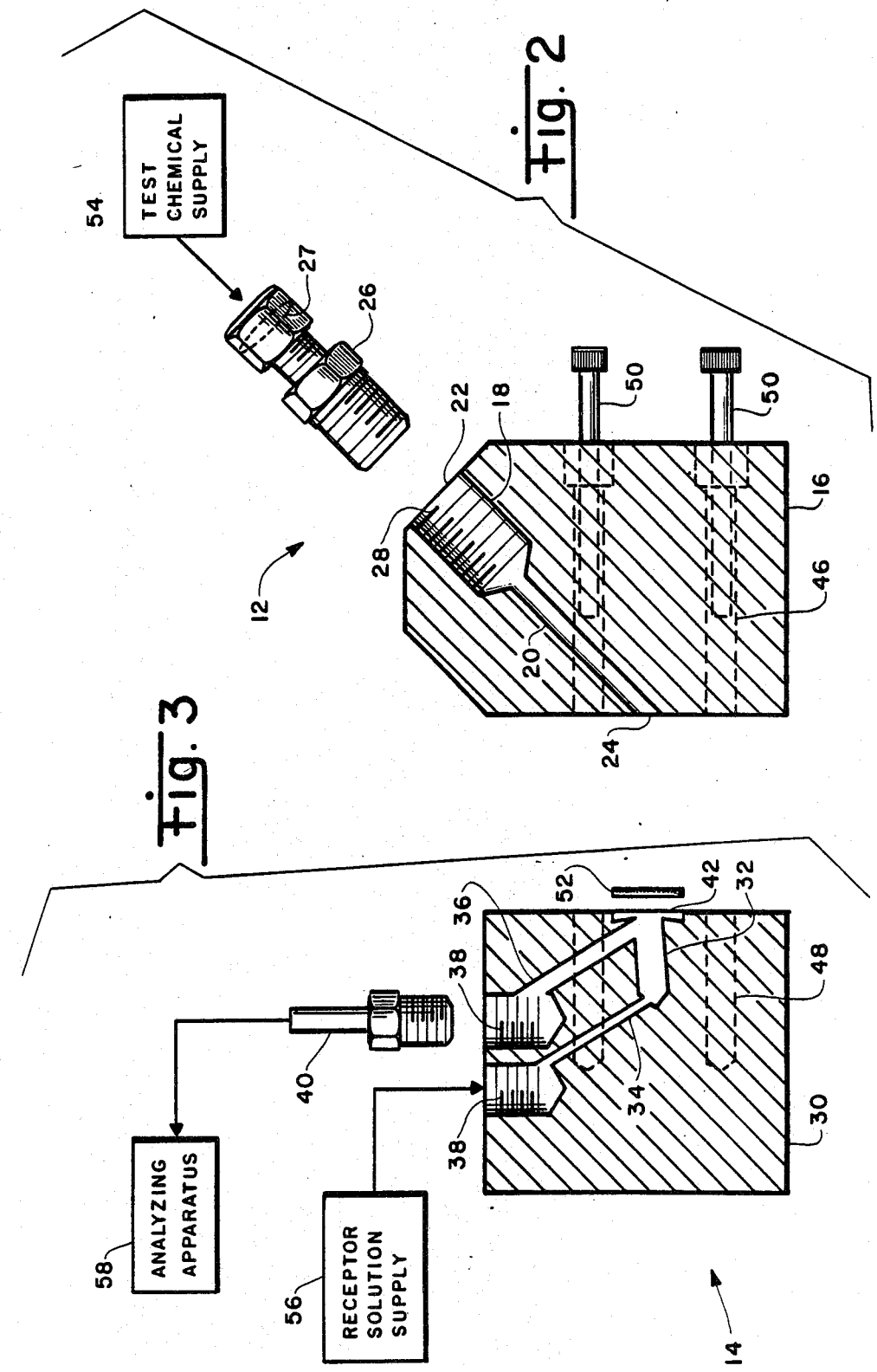

FLOW THROUGH DEVICE FOR DETERMINATION OF THE PENETRATION RATE OF CHEMICALS ACROSS BIOLOGICAL MEMBRANES IN VITRO

RIGHTS OF THE GOVERNMENT

The invention described herein may be manufactured and used by or for the Government of the United States for all governmental purposes without the payment of any royalty.

BACKGROUND OF THE INVENTION

The present invention relates generally to instruments for determining penetration rates through a membrane, and more specifically to an instrument for determining the penetration rate of chemicals through biological membranes in vitro.

The rate of penetration of chemicals through biological membranes is an important factor in studying the possible harmful effects of various chemicals that come into contact with the skin. The determination of penetration rates is particularly important in determining exposure limits for workers in the pharmaceutical, pesticide and other chemical industries.

Penetration rates are generally determined with an instrument that places a selected membrane between a receptor solution and a selected test chemical. After a period of time, the receptor solution is analyzed for the presence of any test chemical that has penetrated the membrane. Present instruments for determining penetration rates are generally made of glass and are fragile, difficult to use, and unreliable. A particular problem with present instruments is that chambers for flowing receptor solution past the membrane allow bubbles to become stalled or trapped inside the chambers, thus interfering with the reliability and reproducibility of the results. This is particularly demonstrated in that present instruments show markedly different test results when tapped or shaken to free trapped bubbles.

Another problem with present instruments is membrane viability. Many present instruments do not provide for the delivery of glucose or other nutrients to maintain the viability of the biological membrane under test to ensure test results more closely related to that of living tissue.

It is seen, therefore, that there is a need for an improved test instrument for determining in vitro the penetration rate of chemicals across biological membranes without the problems of prior art instruments.

It is, therefore, a principal object of the present invention to provide a test instrument for determinig in vitro the penetration rate of chemicals across biological membranes that prevents the trapping or stalling of bubbles in the receptor solution and that provides consistent reproducible test results.

It is another object of the present invention to provide a test instrument for determining in vitro the penetration rate of chemicals across biological membranes that maintains the viability of the tested membrane.

It is a feature of the present invention that it provides for automatically stretching the biological membrane taut over the opening to the reservoir solution chamber.

It is another feature of the present invention that the temperature under which penetration tests are conducted may be conveniently controlled by simple placement of the entire apparatus into a standard, commercially available, dry temperature bath.

SUMMARY OF THE INVENTION

The present invention provides an instrument for determining penetration rates of test chemicals through a biological membrane that provides reliable and reproducible results. The unique discovery of the present invention is a chamber design that avoids completely the bubble entrapment problems associated with present instruments, and the provision of a structure that ensures the test membrane is kept taut over its tested area.

Accordingly, the present invention is directed to an instrument for determining penetration rates through a membrane comprising a reservoir assembly and a receptor assembly. The reservoir assembly comprises a housing with a cavity having an inlet at its upper surface and an outlet at its front surface. The receptor assembly comprises a housing with a substantially horizontal, but slightly tilted to prevent trapped bubbles, receptor solution chamber, a receptor solution inlet bore, a receptor solution outlet bore, and a membrane holding compartment at the open end of the receptor solution chamber formed as a depression in the front face of the receptor housing. Fasteners attached the front faces of the reservoir and receptor housings so that the receptor solution chamber opening and membrane holding chamber may connect with the outlet of the reservoir cavity.

The membrane holding compartment depression is cylindrical and coaxial with the open end of the receptor solution chamber. The depth of the membrane holding compartment depression may taper from a lesser depth at the circumference of the open end of the receptor solution compartment to a greater depth at the circumference of the membrane holding compartment, whereby a force fastening the reservoir front surface to the receptor front surface will stretch the membrane taut over the open end of the receptor solution chamber.

The invention also includes the cross-sectional area of the receptor solution inlet bore being less than the cross-sectional area of the outlet bore.

The invention further includes structure for attaching fittings to the housing bores and a septum fitting to the test chemical cavity.

The invention additionally includes the method performed by the disclosed apparatus of providing a tilted receptor solution chamber, or sizing the receptor solution chamber inlet smaller than the chamber outlet; and, of tapering the front of the back of the membrane holding compartment to stretch the membrane taut over the open end of the receptor solution chamber.

DESCRIPTION OF THE DRAWINGS

The present invention will be more clearly understood from a reading of the following detailed description in conjunction with the accompanying drawings wherein:

FIG. 1 is a perspective view of an apparatus for determining the penetration rate of chemicals across a biological membrane according to the teachings of the present invention;

FIG. 2 is a side cross-sectional view of the reservoir assembly of the apparatus of FIG. 1 including a side view of a rubber septum fitting for test chemicals; and, FIG. 3 is a side cross-sectional view of the receptor assembly of the apparatus of FIG. 1 including a side view of a fitting for receptor solution.

DETAILED DESCRIPTION

Referring now to FIG. 1 of the drawings, there is shown a perspective view of an apparatus 10 for determining in vitro the penetration rate of chemicals across a biological membrane according to the teachings of the present invention. The apparatus comprises two primary sections: a reservoir assembly 12 for holding a supply of a test chemical; and, a receptor assembly 14 for holding a sample of the biological membrane to be tested and for supplying a constant flow of receptor solution for receipt and later analysis for the presence of any test chemical that penetrates the membrane. Reservoir assembly 12 comprises a housing 16 enclosing a cavity 18 for holding the supply of test chemical. Cavity 18 comprises a variable diameter bore 20 that runs from a test chemical inlet 22 at the top of reservoir assembly 12 to an outlet 24 at the front of reservoir assembly 12. A septum fitting 26, shown in side view with FIG. 2's more detailed side cross-sectional view of the reservoir assembly 12, provides, as is more fully explained below, a means for injecting and holding inside cavity 18 a reservoir of test chemical (solid, liquid or gas), obtained from test chemical supply 54. Septum fitting 26 includes a septum 27 and is attached to reservoir assembly 12 by machine threads 28.

Receptor assembly 14, shown in additional detail in the cross-sectional side view of FIG. 3, comprises a housing 30 enclosing a chamber 32, for passage of receptor solution from receptor solution supply 56, having an inlet through bore 34 and an outlet through bore 36. Chamber 32 opens into membrane holding compartment 42. Bores 34 and 36 each include machine threads 38 for receipt of receptor solution fittings 40, only one of which is shown in the figure. Receptor housing 30 includes a bore 60 for receipt of a temperature probe.

Both reservoir housing 16 and receptor housing 30 include cooperating bolt holes 46 and 48 for receipt of bolts 50 which, when tightened, securely fasten the front of reservoir assembly 12 to the front of receptor assembly 14. FIG. 1 shows only one of four bolt holes 48 and suggests three of four bolt holes 46 to avoid confusing the drawing with too many dashed lines.

Chamber 32 slopes upward from its closed end inside receptor housing 30 to its open end at membrane holding compartment 42. The embodiment shown incorporates a slope of about 5 degrees which has successfully prevented any bubbles in the receptor solution from becoming trapped or stalled inside chamber 32. With the placement of outlet bore 36 at the top of the open end of chamber 32, and the sizing of inlet bore 34 smaller than that of outlet bore 36, as both are shown in the figures, the flow of receptor solution across the membrane to be tested is regular and smooth so that repeated tests of membrane penetration with various test chemicals are consistently reproducible.

Membrane holding compartment 42 is formed as a cylindrical depression in the front face of receptor housing 30. The depth of the depression increases from its intersection with the receptor solution chamber 32 to the outer circumference of the cylindrical depression, thus forming a truncated cone. This structure ensures that a membrane sample 52 will be stretched taut over the open end of receptor solution chamber 40 when pressed into place by the force attaching together the front faces of reservoir housing 16 and receptor solution housing 30.

To use the invention, a biological membrane sample 52 is prepared by pressing a hole cutter into a section of the membrane to be tested to obtain a circular sample of the approximate diameter of membrane holding compartment 42. The membrane sample 52 is inserted into membrane holding compartment 42 and reservoir housing 16 and receptor housing 30 are bolted together. Next, test chemical reservoir cavity 18 is filled with test chemical from a test chemical supply 54. For liquids and gases, a syringe is filled from test chemical supply 54, the syringe needle inserted through septum 27 and the liquid or gas to be tested for penetration injected into cavity 18. Upon removal of the syringe needle, septum 27 seals the test chemical inside test chemical cavity 18. Receptor solution from a receptor solution supply 56 is supplied through a fitting 40 (not shown) at the receptor solution inlet bore 34, flowed through the receptor solution chamber 32 and past the membrane sample 52, and then removed through a fitting 40 at outlet bore 36. The removed receptor solution is supplied to any wellknown in the art analyzing apparatus for determining the amount of test chemical that penetrated membrane sample 52 over a period of time. Alternatively, during testing the receptor solution may remain static inside the receptor solution chamber 32, rather than dynamically flowing, and the receptor solution tested for the presence of the test chemical after a measured period of time.

The receptor solution may include glucose or other nutrients to maintain the viability of membrane sample 52.

A significant feature of the present invention is its ability to provide consistently reproducible results, thus allowing the results of tests performed by different researchers at different times to be usefully compared. For comparing test results provided by different researchers using different sizes or variations of the disclosed apparatus, the cross-sectional area of the test chemical cavity outlet 24 is the primarily critical dimension for comparison. The other parameters and calculations for comparing results obtained from different apparatus are well known to those with skill in the art.

It is understood that certain modifications to the invention as described may be made, as might occur to one with skill in the field of the invention, within the intended scope of the claims. Therefore, all embodiments contemplated have not been shown in complete detail. Other embodiments may be developed without department from the spirit of the invention or from the scope of the claims.

I claim:

1. An instrument for determining penetration rates through a membrane, comprising:
    (a) a reservoir housing having an upper surface and a front surface;
    (b) a cavity inside the reservoir housing, the cavity having an inlet at the reservoir housing upper surface and an outlet at the reservoir housing front surface;
    (c) a receptor housing having an upper surface and a front surface;
    (d) a substantially horizontal first bore inside the receptor housing, the first bore having an upper surface, a lower surface, a closed end inside the receptor housing, and an open end at the receptor housing front surface, the open end sufficiently higher than the closed end so that bubbles in a fluid inside the first bore will move toward the open end;

(e) a second bore inside the receptor housing, the second bore having an inlet at the receptor housing upper surface and an outlet open to the first bore substantially at the closed end of the first bore;

(f) a third bore inside the receptor housing, the third bore having an outlet at the receptor housing upper surface and an inlet open to the first bore substantially at the open end of the first bore at its upper surface;

(g) a membrane holding compartment in the receptor housing, the membrane holding compartment comprising a depression in the receptor housing front surface, the depression surrounding the open end of the first bore; and, (h) fastening means for securing the reservoir housing front surface to the receptor housing front surface, whereby the first bore and the membrane holding compartment are operatively interconnected with the cavity outlet.

2. The instrument for determining penetration rates through a membrane according to claim 1, wherein the membrane holding compartment depression is substantially cylindrical and substantially coaxial with the open end of the first bore.

3. The instrument for determining penetration rates through a membrane according to claim 2, wherein the depth of the membrane holding compartment depression tapers from a lesser depth at the circumference of the open end of the first bore to a greater depth at the circumference of the membrane holding compartment, whereby a force applied by the fastening means in securing the reservoir housing front surface to the receptor housing front surface against a membrane inside the membrane holding compartment will stretch the membrane taut over the open end of the first bore.

4. The instrument for determining penetration rates through a membrane according to claim 1, wherein the cross-sectional area of the second bore is less than the cross-sectional area of the first bore.

5. The instrument for determining penetration rates through a membrane according to claim 1, wherein the first bore has an axis which rises from the closed end to the open end at an angle of about four degrees to about six degrees from the horizontal.

6. The instrument for determining penetration rates through a membrane according to claim 1, wherein:
(a) the cavity inlet further comprises first means for attaching a fitting to the cavity inlet;
(b) the second bore inlet further comprises second means for attaching a fitting to the second bore inlet; and,
(c) the third bore inlet further comprises third means for attaching a fitting to the third bore inlet.

7. The instrument for determining penetration rates through a membrane according to claim 5, further comprising a septum fitting attached to the cavity inlet.

8. The method of determining penetration rates of a test chemical through a membrane into a receptor solution, comprising the steps of:
(a) providing a chamber having an open end for flowing the receptor solution past the membrane to be tested;
(b) tilting the chamber so that bubbles in the receptor solution flow toward the open end;
(c) providing a membrane holding chamber for holding the membrane against the open end of the chamber;
(d) providing a cavity for holding the test chemical against the membrane;
(e) providing an inlet to the chamber for supplying the flowing receptor solution and an outlet located substantially at the upper surface of the open end of the chamber for exiting the receptor solution; and,
(f) analyzing the receptor solution for the presence of the test chemical.

9. The method of determining penetration rates of a test chemical through a membrane into a receptor solution according to claim 8, further comprising the step of sizing the cross-sectional area of the inlet to the chamber smaller than the cross-sectional area of the chamber outlet.

10. The method of determining penetration rates of a test chemical through a membrane into a receptor solution according to claim 8, further comprising the step of tapering the open end of the chamber in the shape of a truncated cone so that the membrane, when held between the chamber and the cavity, is stretched taut against the chamber open end.

* * * * *